US011654226B2

(12) United States Patent
Mills et al.

(10) Patent No.: US 11,654,226 B2
(45) Date of Patent: May 23, 2023

(54) REMOVABLE INLET MANIFOLD FOR A MEDICAL WASTE COLLECTION SYSTEM

(71) Applicant: Medline Industries, Inc., Northfield, IL (US)

(72) Inventors: Andrew Mills, Highland Park, IL (US); David Noskowicz, Spring Grove, IL (US); Brian Barkeley, Huntington Beach, CA (US); Zachary Zott, Chicago, IL (US); Stuart Mintz, Glenview, IL (US)

(73) Assignee: Medline Industries, LP, Northfield, IL (US)

( * ) Notice: Subject to any disclaimer, the term of this patent is extended or adjusted under 35 U.S.C. 154(b) by 0 days.

(21) Appl. No.: 17/387,942

(22) Filed: Jul. 28, 2021

(65) Prior Publication Data

US 2021/0353848 A1  Nov. 18, 2021

Related U.S. Application Data

(63) Continuation of application No. 16/825,573, filed on Mar. 20, 2020, now Pat. No. 11,090,414, which is a
(Continued)

(51) Int. Cl.
*A61M 1/00* (2006.01)
(52) U.S. Cl.
CPC ............... *A61M 1/63* (2021.05); *A61M 1/79* (2021.05); *Y10T 137/794* (2015.04)
(58) Field of Classification Search
CPC ........ A61M 1/63; A61M 1/79; Y10T 137/794
See application file for complete search history.

(56) References Cited

U.S. PATENT DOCUMENTS 2,760,509 A    8/1956 Side
4,306,557 A   12/1981 North
(Continued)

FOREIGN PATENT DOCUMENTS

WO    2005042061 A1    5/2005
WO    2007103842 A2    9/2007

OTHER PUBLICATIONS

"Waste Management—Neptune 2: Stryker," Stryker 1998-201_. Web Jul. 15, 2016. <<http://www.stryker.com/en-us/products/SurgicalEquipment/WasteManagement/Neptune2/index.htm>>.
(Continued)

*Primary Examiner* — Patrick C Williams
(74) *Attorney, Agent, or Firm* — Gurr Brande & Spendlove, PLLC.; Robert Spendlove

(57) ABSTRACT

A removable manifold for a medical/surgical waste collection system. The manifold is dimensioned to be mounted to a receiver integral with the system. The manifold includes at least one tube through which waste is drawn into a manifold cage. The tube extends through an inlet port into a void space internal to the manifold cage at an angle. The tube exits the manifold cage and centered along an axis that is off center to the longitudinal axis of the manifold cage where it engages a complementary valve internal to the receiver. The valve regulates flow between the receiver and the down line components of the waste collection system. The valve is normally closed. When the manifold is fitted to the receiver the tube engages the valve and rotation of the manifold moves the valve to the open position allowing fluid flow from the manifold and receiver to the downstream components of the system.

18 Claims, 11 Drawing Sheets

Related U.S. Application Data continuation of application No. 15/983,510, filed on May 18, 2018, now Pat. No. 10,617,799.

(60) Provisional application No. 62/507,943, filed on May 18, 2017.

(56) References Cited

U.S. PATENT DOCUMENTS

| | | |
|---|---|---|
| 4,393,879 A | 7/1983 | Milgrom |
| 4,744,785 A | 5/1988 | Rosenthal et al. |
| 4,863,446 A | 9/1989 | Parker |
| 5,624,417 A | 4/1997 | Cook et al. |
| 6,027,490 A | 2/2000 | Radford et al. |
| 6,331,246 B1 | 12/2001 | Beckham et al. |
| 7,615,037 B2 | 11/2009 | Murray et al. |
| 8,216,199 B2 | 7/2012 | Murray et al. |
| D678,502 S | 3/2013 | Schmidt et al. |
| D678,503 S | 3/2013 | Schmidt et al. |
| D678,504 S | 3/2013 | Schmidt et al. |
| 8,518,002 B2 | 8/2013 | Murray et al. |
| 8,882,793 B2 | 11/2014 | Dubois et al. |
| 8,915,897 B2 | 12/2014 | Murray et al. |
| 9,795,723 B2 | 10/2017 | Gavlak et al. |
| 10,603,416 B1 | 3/2020 | Zollinger et al. |
| 2005/0139532 A1 | 6/2005 | Hershberger et al. |
| 2005/0171495 A1 | 8/2005 | Austin et al. |
| 2008/0243029 A1 | 10/2008 | Howard et al. |
| 2011/0278295 A1 | 11/2011 | Martini et al. |
| 2011/0278296 A1 | 11/2011 | Martini et al. |
| 2015/0105740 A1 | 4/2015 | Reasoner et al. |
| 2017/0043064 A1 | 2/2017 | Reasoner et al. |

OTHER PUBLICATIONS

International Search Report; International Patent Application No. PCT/US2018/033391; Medline Industries, Inc.; dated Dec. 4, 2018.

Written Opinion of the International Searching Authority; International Patent Application No. PCT/US2018/033391; Medline Industries, Inc.; dated Dec. 4, 2018.

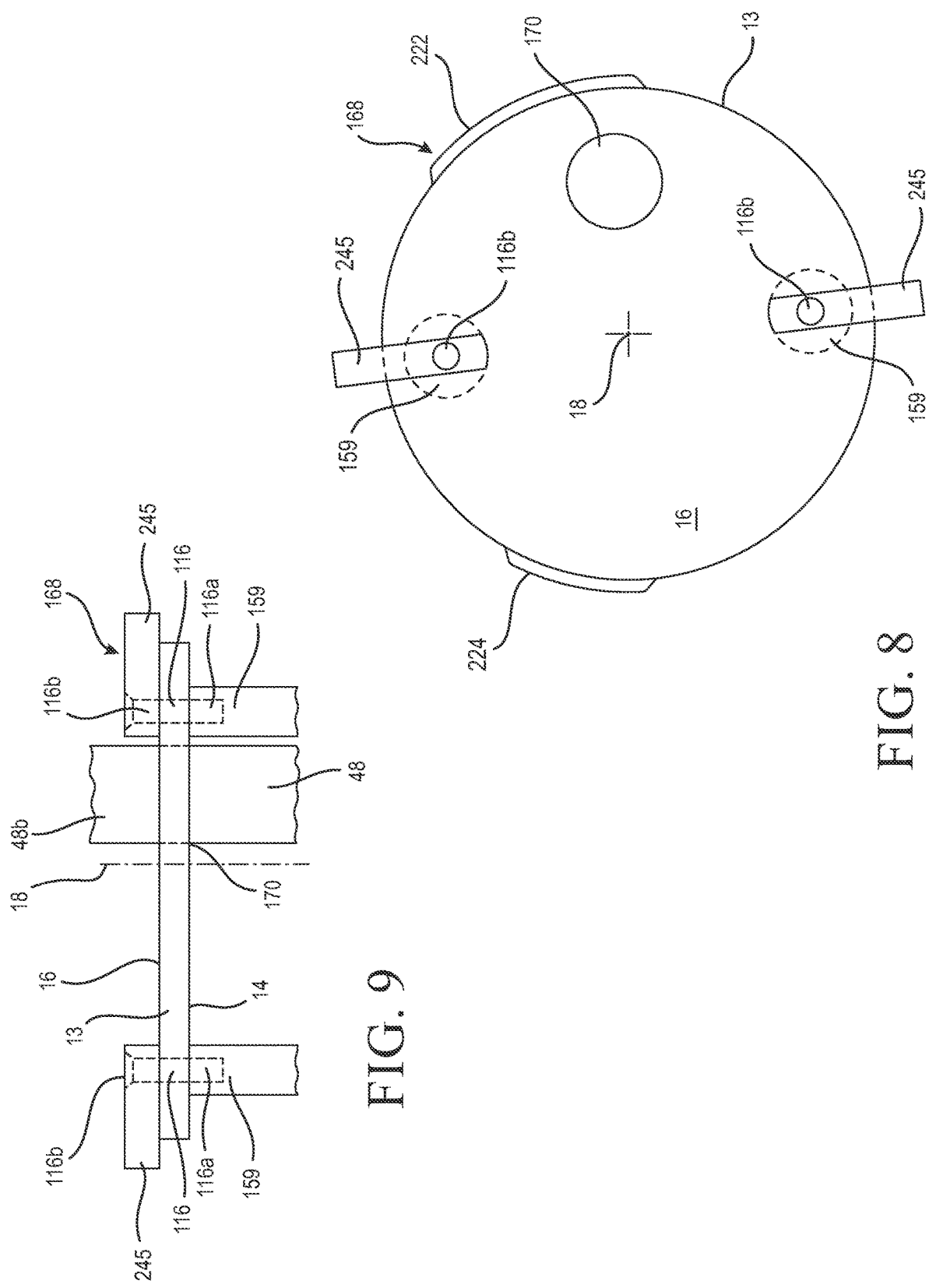

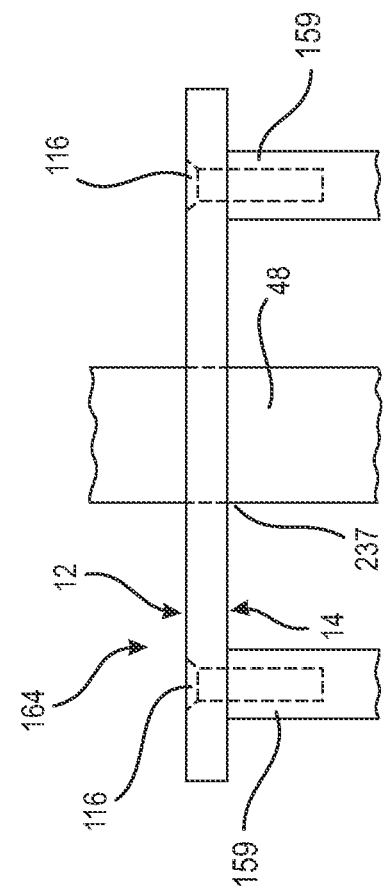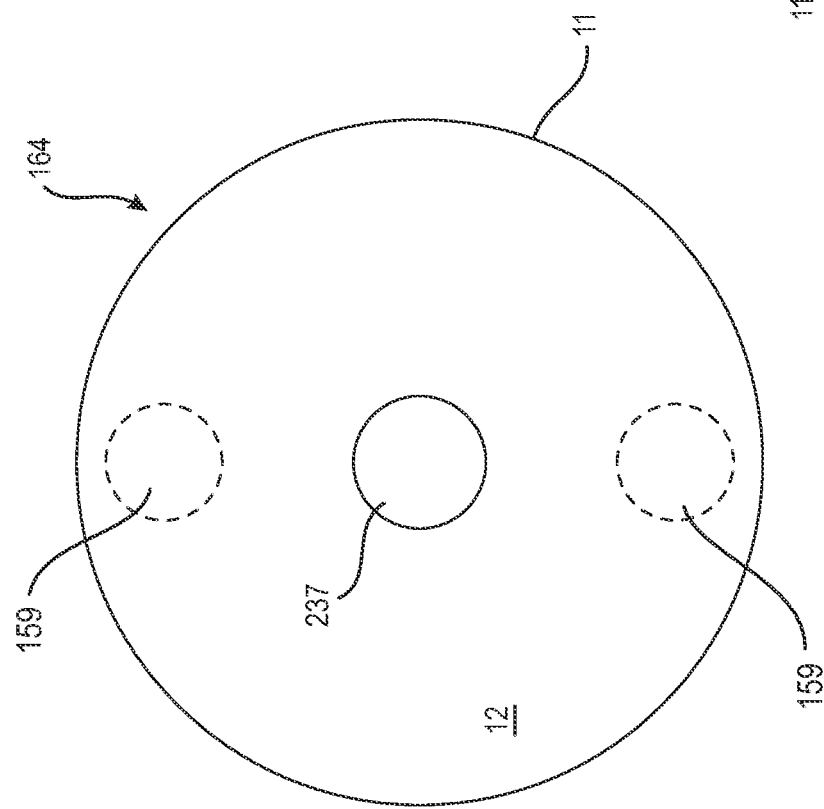

REMOVABLE INLET MANIFOLD FOR A MEDICAL WASTE COLLECTION SYSTEM

RELATED APPLICATIONS

This application is a continuation of U.S. patent application Ser. No. 16/825,573, filed Mar. 20, 2020, entitled "REMOVABLE INLET MANIFOLD FOR A MEDICAL WASTE COLLECTION SYSTEM," which is a continuation of U.S. patent application Ser. No. 15/983,510, filed on May 18, 2018, and issued as U.S. Pat. No. 10,617,799 on Apr. 14, 2020, which claims priority to and benefit of U.S. Provisional Patent Application No. 62/507,943, filed on May 18, 2017, each of which is incorporated herein by reference.

FIELD OF THE INVENTION

This invention relates to a waste collection system with a removable intake manifold.

BACKGROUND OF THE INVENTION

A byproduct of the performance of some medical and surgical procedures is the generation of liquid, semi-solid and solid waste. This waste includes body fluids, such as blood, and irrigating solution that are introduced to the body site at which the procedure is performed. Solid and semi-solid waste generated during a procedure includes bits of tissue and small pieces of the surgical material that may be left at the site. Ideally, the waste is collected upon generation so it neither fouls the surgical site nor becomes a biohazard in the operating room or other location at which the procedure is being performed.

A number of systems are available for use by surgical personnel for collecting this waste as it is generated. Generally, these units include a suction source, tubing that extends from the suction source and a containment unit between the tubing and the suction source. When the system is actuated, waste is drawn through the opening end of the tubing. The suction draws the waste through the tubing so that it flows into and is stored in the containment unit.

One system includes a mobile unit that includes a suction pump and a canister. Tubing is connected to the canister through a removable manifold. Since this unit is mobile, it can be positioned in relatively close proximity to the patient on whom the procedure is being performed. This reduces the extent to which the suction tubing, which invariably also functions as operating room clutter, is present around the surgical personnel.

Another feature of this system is the removable intake manifold. The manifold includes an optional filter element that traps large bits of solid matter which can potentially clog the down line components of the system. Moreover, the manifold is formed from material that makes it possible to provide the manifold as a single use item. After use of the system, effort does not have to be spent sterilizing the manifold. Instead, personnel handling the used manifold only need to contact the outer surface of this component, minimizing the extent to which individuals potentially come into contact with waste material.

Use of the above system significantly reduces the extent to which medical/surgical personnel are exposed to potentially hazardous medical waste. Nevertheless, there are some disadvantages associated with known waste collection systems. For example, a manifold can extend directly into the canister in which the waste is stored. Small droplets of waste can adhere to the sides of the manifold. Upon removal of the manifold from the mobile unit, adhered liquid is essentially an uncontained waste in the surrounding environment. If the liquid is not immediately wiped off the manifold, it can potentially fall off the manifold and be added waste matter that needs to be cleaned off a floor or other surface.

In known systems, the filter of the manifold does more than trap the small bits of solid that can clog the down stream components of the mobile unit. The filter also traps an appreciable volume of semi-solid state waste. Thus, care must be taken when removing the manifold to ensure that this waste does not escape.

Moreover, medical personnel sometimes visually monitor the volume of material collected by the mobile unit canister. This monitoring is performed to provide a rough estimate of the volume of fluid withdrawn from the patient during a procedure. If an appreciable amount of liquid remains trapped in the manifold, the accuracy of the quick visual estimate of collected stored fluid can be adversely affected.

Further, in known systems, upon removal of the manifold from the canister, the port on which the manifold was seated opens to the ambient environment. Material collected in the canister is known to emit smells that are typically considered unpleasant. Thus, the removal of the manifold results in the release of these odors into the environment.

Also, the air and other fluids flowing through the waste collection system, both the manifold and mobile unit, can generate noise. This noise contributes to the unwanted background noise in an operating room.

SUMMARY OF THE INVENTION

This invention is directed to a new and useful intake manifold for use with a system for collecting surgical and medical waste. The intake manifold is connected to suction tubes of the system. The manifold is removably coupled to a manifold receiver, an integral part of the waste collection unit. The manifold is designed to minimize the release of uncontained fluids upon removal and replacement of the manifold.

In embodiments of the present application, the intake manifold includes a cylindrical cage. At one end, an inlet port receives a suction tube. The opposite end of the cage has a through opening through which the suction tube extends. When the manifold is seated in the receiver of mobile waste collection system, the tube extending through the opening joins a tubular boss that is part of the receiver.

The receiver boss extends from a valve, also part of the receiver. Normally, this valve closes a fluid conduit that extends into a canister into which the waste is stored. As part of the preparation of the system for operation, the manifold is properly seated in the receiver. The manifold engages a complementary drive member integral with the valve. Thus, the placement of the manifold in the receiver displaces the valve into the open state. There is an unrestricted fluid path from the manifold to the complementary conduit that leads to the canister.

When the manifold is removed, the valve returns to the closed state. The return of the valve to the closed state blocks the release of unpleasant vapors from the canister when the manifold is removed from the system.

In some embodiments, external to the manifold is an optional filter basket. The filter basket both traps large bits of solid matter that are part of the waste stream while allowing substantially the whole of the liquid component of the stream to flow therethrough. Upon completion of a surgical procedure, only a minimal amount of liquid state waste, the type that is the most prone to leakage, is left in the manifold.

BRIEF DESCRIPTION OF THE DRAWINGS

The invention is pointed out with particularity in the claims. The above and further features and advantages of the invention are understood by the following Detailed Description taken in conjunction with the accompanying drawings in which:

FIG. 8 is a top view of the manifold cage cap plate of FIG. 6;

FIG. 9 is a side view of the manifold cage cap plate of FIG. 8;

FIG. 10 is a bottom view of the manifold base plate of FIG. 6;

FIG. 11 is a side view of the manifold cage base plate of FIG. 10;

DETAILED DESCRIPTION

Figure 1:
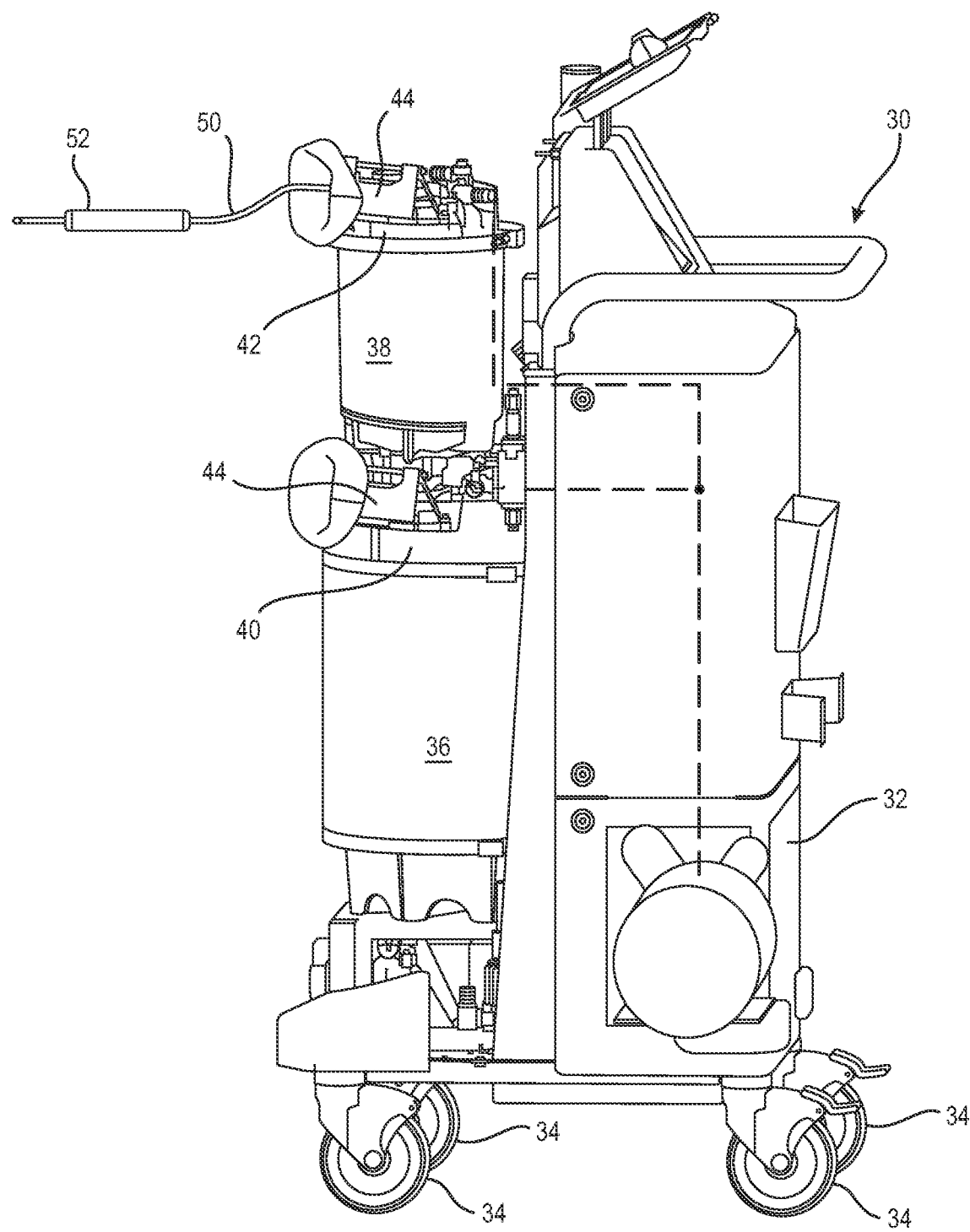
FIG. 1 is a side view of a medical/surgical waste collection system.

Before describing in detail embodiments that are in accordance with the present invention, it should be observed that the embodiments reside primarily in combinations of apparatus components and method steps for a manifold for removable connection to a medical/surgical waste collection unit. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In describing the embodiments herein in detail and referring to the drawings, like numbers indicate like parts throughout the figures. As used in the description herein and throughout the claims, the following terms take the meaning explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual relationship or order between such entities or actions.

FIG. 1 illustrates a waste collection system 30 known in the art. System 30, sometimes referred to as a mobile unit, includes a base 32. The cover and door assemblies that normally conceal the components are mobile unit 30 are not present in FIG. 1 so that these components can be seen. Wheels 34 attached to the bottom of the base 32 provide the system with mobility. Two canisters 36 and 38 are mounted to the base 32. A first one of the canisters, canister 36, has a relatively large interior volume, between approximately 10 and 40 liters. The second canister, canister 38, has a smaller volume, between approximately 1 and 10 liters. Each canister 36 and 38 has a cap 40 and 42, respectively. Attached to each canister cap 40 and 42 is a manifold receiver 44.

Figure 2:
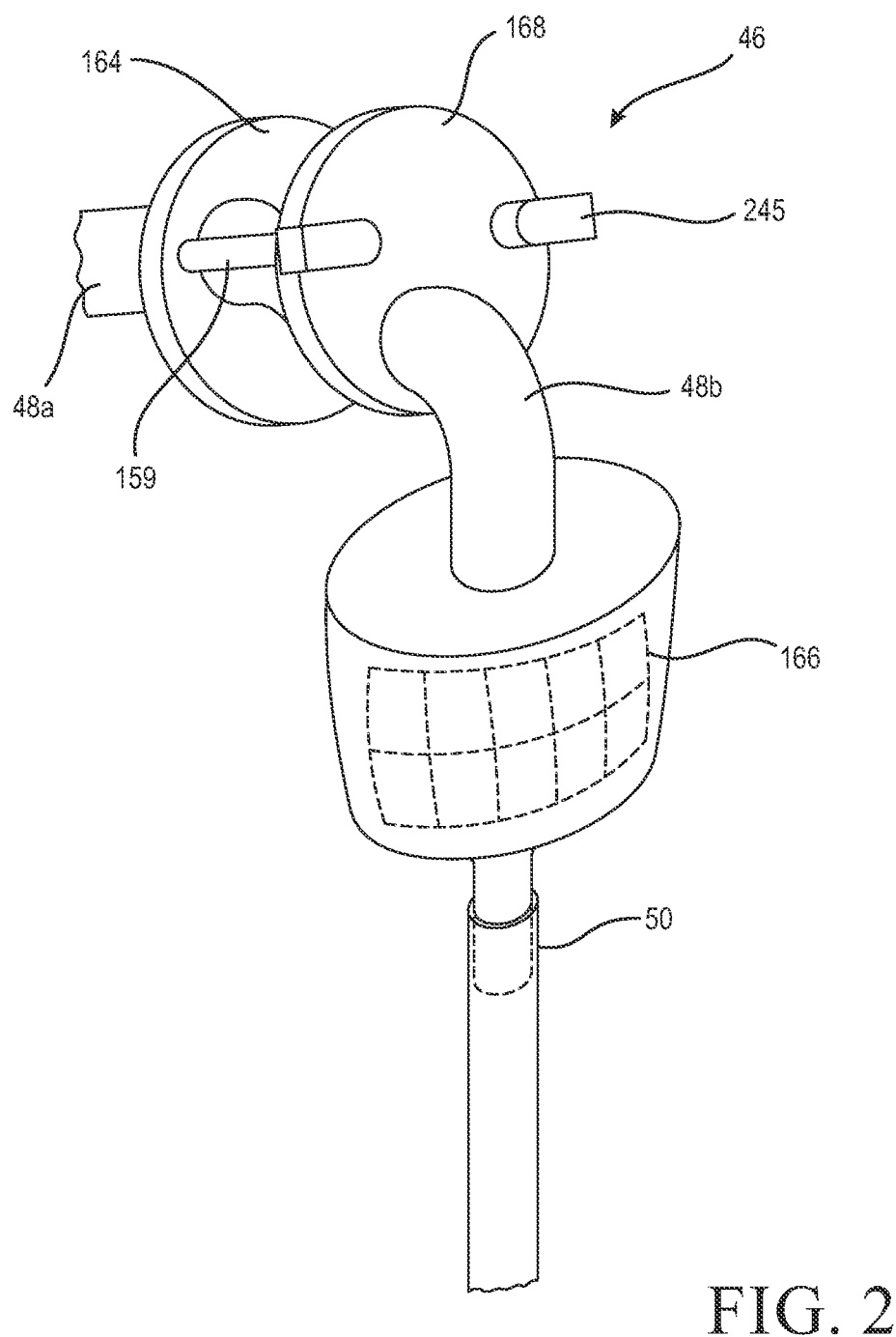
FIG. 2 is a front perspective view of a manifold assembly in accordance with embodiments of the present invention.

FIG. 2 illustrates an embodiment of a manifold assembly in accordance with the present invention. As described further below, the manifold assembly may include a manifold or manifold cage 46 that comprises a base plate 164, a cap plate, and one or more ribs 159. The manifold assembly may also comprise a filter assembly having a filter basket 166. The manifold assembly may further include a tube 48, which receives a separate suction line 50. The distal end of each suction line 50 is attached to a suction applicator 52 (FIG. 1). ("Distal," it is understood means towards the surgical site at which the suction is applied. "Proximal" means away from the surgical site.) While in FIG. 1, suction applicator 52 is shown as handpiece specifically and solely designed to apply suction, it should be understood that this is exemplary, not limiting. Sometimes the suction applicator 52 is built into another surgical tool, such as an endoscope or ablation tool, applied to surgical site to accomplish a task other than applying suction.

Figure 3:
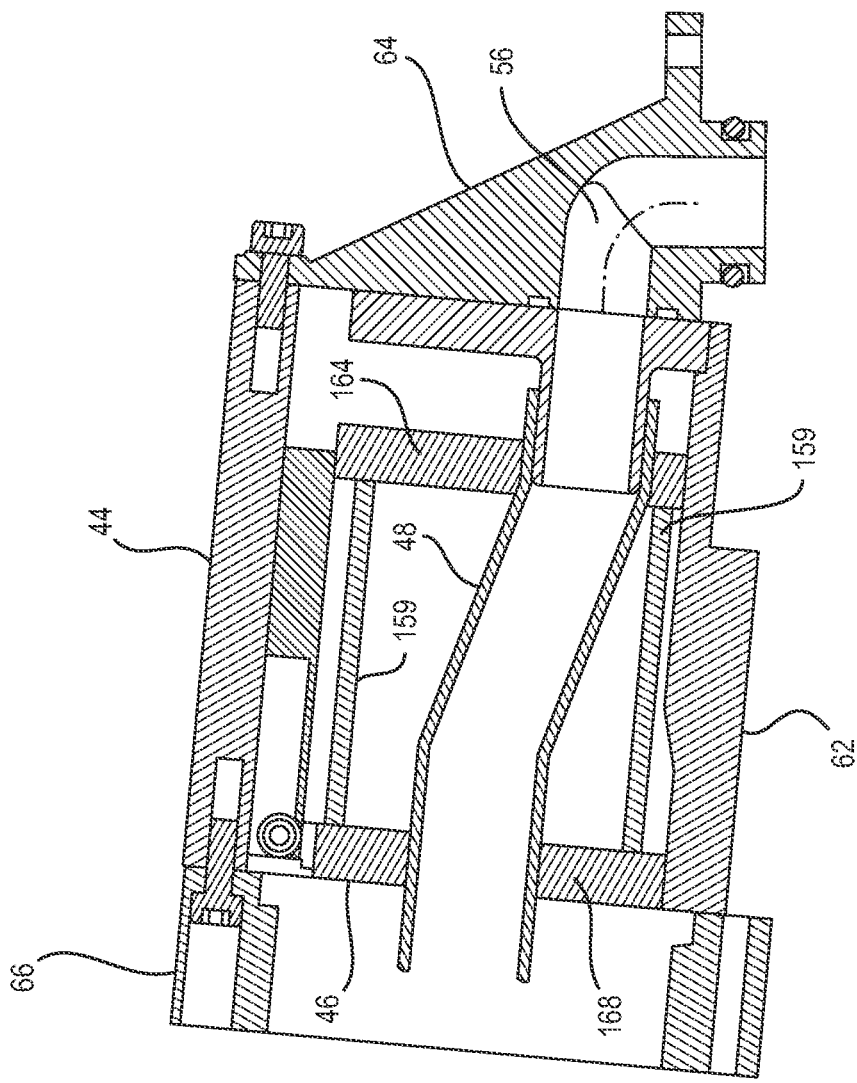
FIG. 3 is a cross sectional view showing a manifold seated in a manifold receiver in accordance with embodiments of the present invention.
Figure 4:
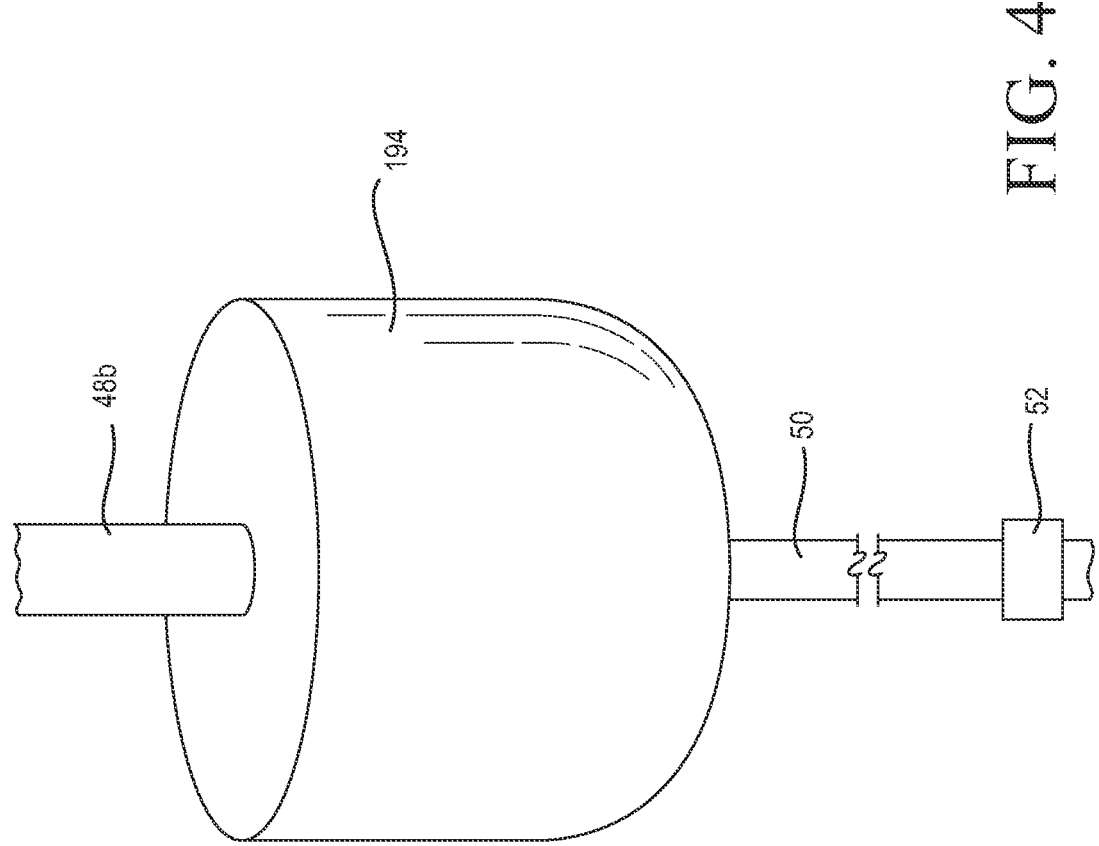
FIG. 4 is a front elevation view of a filter assembly in accordance with embodiments of the present invention.

As illustrated in FIG. 3, the manifold 46 is removably seated in each manifold receiver 44. A conduit 56 is positioned internal to each manifold receiver 44. Conduit 56 functions as a fluid communications path from the manifold 46 into the canister 36 or 38 with which the receiver is associated. The manifold receiver 44 may comprise a lock ring 66 attached to a distal front end of manifold receiver housing 62. The manifold receiver may also include an adaptor 64 that holds the manifold receiver housing 62 to the associated canister cap 40 or 42. The conduit 56 may pass through the manifold adaptor 64 to provide a flow path from the manifold receiver housing 62 into the associated canister 36 or 38.

Figure 5:
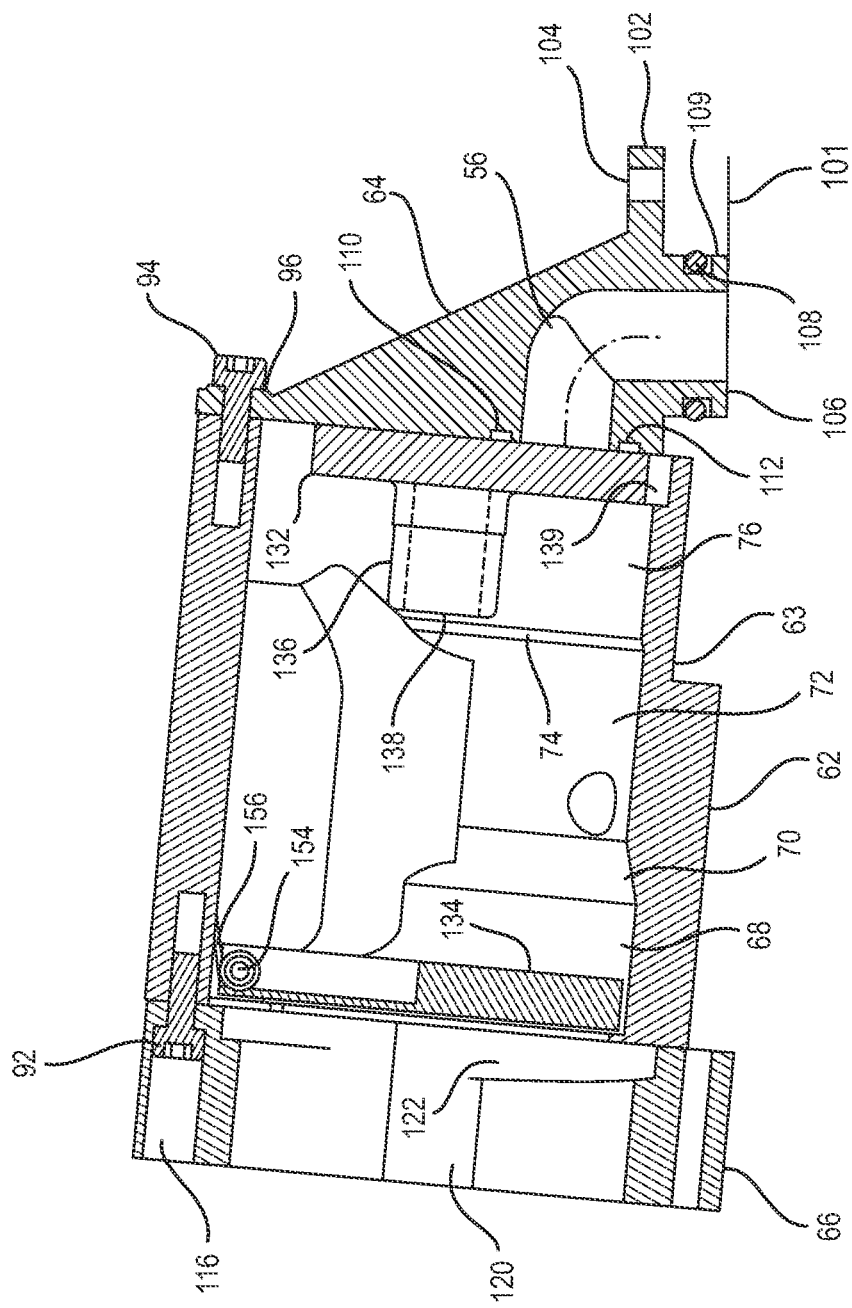
FIG. 5 is a cross sectional view of the manifold receiver when empty.

In accordance with embodiments of the manifold receiver shown in FIG. 5, manifold receiver housing 62 has a generally cylindrical shape. The proximal end of the manifold receiver has an outer surface 63 that is stepped inwardly relative to the more distal outer surface. This spacing facilitates the fitting of the receiver 44 to the associated canister cap 40 or 42.

The lock ring 66 is generally ring shaped. One or more bores 116 extend longitudinally through the ring. Bores 116 receive fasteners 92 used to hold the lock ring 66 to the manifold receiver housing 62. The lock ring 66 comprises one or more slots 120. The lock ring may further comprise grooves 122, each groove contiguous with one of slots 120. Slots 120 and grooves 122 function to retain the lock ring by engaging tabs 222, 224 integral with the manifold 46 travel as is described below. Slots 120 may be the same size or may vary in size to accommodate different size tabs.

A door 134 may be pivotally mounted to manifold receiver housing 62 as best seen in FIG. 5. A pin 154 extends through the manifold receiver housing 62 and through a hole in the door. The pin pivotally holds the door to the manifold housing. A torsion spring 156 is disposed around a section of pin 154 and press against the door 134 and receiver housing 62 to bias the door in a closed position.

The interior diameter of the manifold receiver housing 62 may vary. For example, at the distal end, housing 62 has cylindrical bore 68. Immediately adjacent to the proximal end of bore 68 there is a bore 70. Bore 70 has a diameter that decreases along its length as the distance from bore 68 increases. Bore 70 opens into a second constant diameter bore, bore 72. Bore 72 has a diameter equal to that of the smallest diameter section of bore 70. Proximal to bore 72 manifold receiver housing 62 is formed with a third constant diameter bore, bore 76. Bore 76 has a diameter less than that of bore 72. Between bores 72 and 76 there is a small transition bore 74. Transition bored 74 has a diameter that tapers inwardly from bore 72 to bore 76.

The manifold receiver may also comprise a valve disk 132 that normally covers the opening into conduit 56 formed in the receiver adapter 64. Valve disk 132 is a disk shaped member disposed in the proximal end of the manifold receiver housing 62. Valve disk 132 is formed to have cylindrical boss 136 that extends distally forward into manifold receiver housing bore 76. A bore 138 extends through both boss 136 and the portion of the valve disk from which the boss extends. The valve disk 132 is formed so that the boss is centered along an axis that is radially offset from the axis around which the valve disk rotates. The valve disk 132 also is formed so as to have a notch 139. Notch 139 extends inwardly from the outer perimeter of the valve disk. Relative the center axis of the valve disk 132, notch 139 is located on the side of the disk opposite the side from which boss 136 extends.

An annular slot 110 may also be formed in the distally directed face of manifold receiver adapter 64. Slot 110 is concentric with, surrounds and is spaced away from the opening into conduit 56. A seal 112 may be disposed in slot 110 to seal against a proximal face of valve disk 132. The manifold receiver adapter 64 may also comprise a boss 106. When manifold receiver 44 is mounted to the associated canister cap 40 or 42, boss 106 seats in an opening formed in the cap. An O-ring 108 is seated in a groove 109 that extends circumferentially around the boss. When mobile unit 30 is assembled, O-ring 108 provides a seal between the canister cap and the inserted boss 106 of the manifold receiver 44. The adapter 64 may also include a tab 102 that extends proximally/rearwardly from the base of the adapter. Tab 102 is formed with an opening 104. Opening 104 receives a fastener (not illustrated) that secures the receiver adapter 64 to the canister cap 40 or 42.

Figure 6:
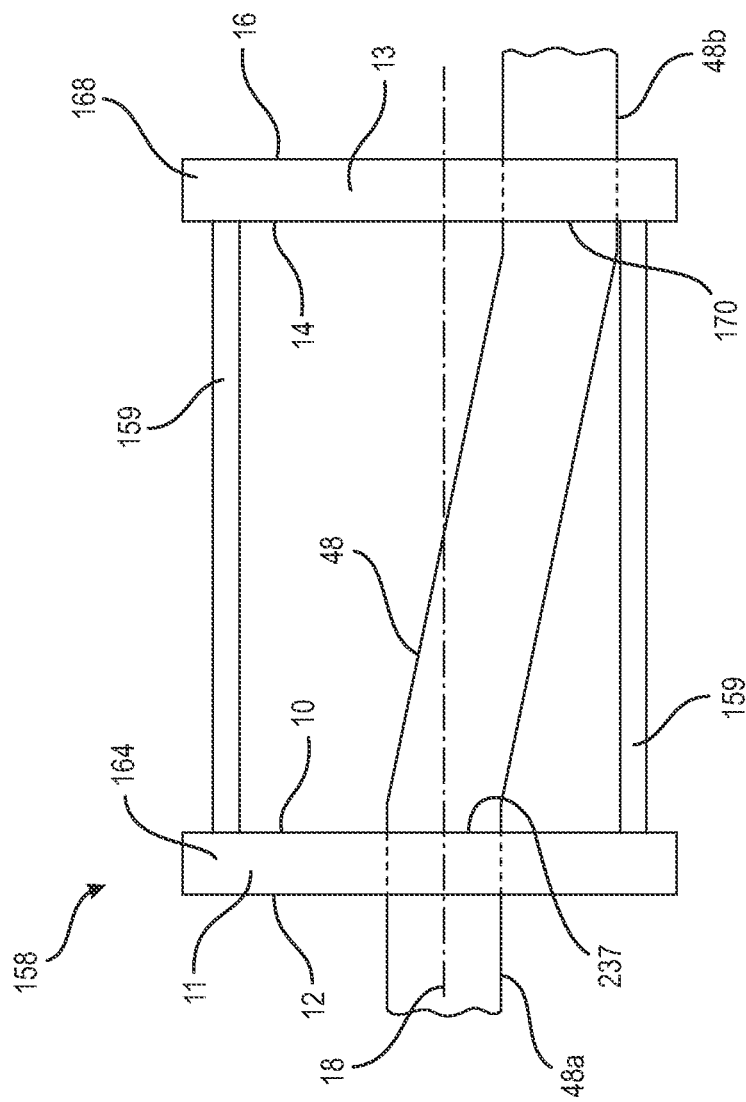
FIG. 6 is a side elevation view of a manifold cage in accordance with embodiments of the present invention.

As see in FIG. 6, the proximal end of the manifold 46 includes a circular base plate 164. The distal end of the manifold includes a circular cap plate 168. Each of plates 164, 168 have an outside planar surface 12, 16, respectively, and an inside planar surface 10, 14, respectively. The inside planar surfaces 10, 14 of each of plates 164, 168 are positioned in parallel spaced relation from one another and are joined by a plurality of ribs 159 positioned along corresponding inside planar edge portions of plates 164, 168. Each of plates 164, 168 and ribs 159 are formed of a rigid material and when joined together comprise a manifold cage 158.

Finger grips 245, as best seen in FIGS. 8-9, extend outwardly from the outside surface 16 of cap plate 168 and extend beyond the perimeter of cap plate 168. Finger grips 245 function as the manifold member to which an individual holds onto in order to insert, rotate and remove the manifold as described in the below procedures.

Finger grips 245 are positioned on the outside surface 16 of cap plate 168 in a location corresponding to the position occupied by a rib 159 in the inside surface 10 of cap plate 164. Alternatively, finger grip 245 may be positioned on any portion of the outside surface 12 of cap plate 168.

Base plate 164 and cap plate 168 include corresponding through bores 116 for receiving fasteners (not shown). Central bores 116a extend partially into each of rib 159 end portions. Through bores 116b extend through end portions of finger grips 245. To assemble manifold cage 158, a fastener enters bore 116b in finger grip 245. The fastener and finger grip 245 are then aligned with corresponding bore 116 on the outside surface 16 of cap plate 168, and the fastener exits on the inside surface 14 of cap plate 168 where partial bore 116a of an end portion of rib 159 receives the portion of the fastener having exited on the inside surface 14 of cap plate 168. Similarly, a fastener enters bore 116 of base plate 164 on the outside surface 12 of base plate 164, and exits on the inside surface 10 of base plate 164, where partial bore 116a of an opposite end portion of rib 159 receives the portion of the fastener having exited on the inside surface 10 of base plate 164. In an alternative embodiment, cage 158 is a unitary structure.

It is understood that manifold cage 158 has a generally cylindrical shape. Manifold cage 158 may also have a tapered cylindrical shape or a truncated conical shape or other shape consistent with the embodiments of the invention.

The manifold cap plate 168, as shown in FIGS. 8-9 includes an opening 170. Cap plate 168 is formed so that opening 170 is centered along an axis that is off center to the longitudinal axis 18 of the cage 158. Cap plate 168 is sized to allow the manifold cage 158 to be disposed in and rotated in receiver housing 62. From opposite side walls 13 of cap plate 168, two bayonet tabs 222 and 224 project radially outwardly. Tabs 222 and 224 are diametrically opposed from each other. Tabs 222 and 224 may, however, extend over different arc lengths. Tab 222 has a relatively large arc; this tab is designed to slip fit into a larger manifold receiver lock ring slot 120. Tab 224 has a shorter arc; this tab is designed to slip fit into a smaller manifold receiver lock ring slot 120.

The manifold base plate 164 is described with reference to FIGS. 10-11. Manifold base plate 164 is circular, and like cap plate 168, is sized to allow the manifold cage 158 to be disposed in and rotated in receiver housing 62. In one embodiment, base plate 164 and cap plate 168 may have the same diameter. In other embodiments, base plate 164 and cap plate 168 may have different diameters, with cap plate 168 being of a larger diameter than based plate 164. In some embodiments, when base plate 164 has a diameter smaller than cap plate 168, a central axis of the base plate 164 may be offset from a central axis of the cap plate 168. In such an embodiment, opening 170 is located along an axis that is off center to the central axis of the cap plate and the longitudinal axis 18 of cage 158. Port 237 is located along an axis that is central to the central axis of the base plate but offset to the longitudinal axis 18 of cage 158. The differing cap and base plate diameters enables port 237 to be joined with bore 138 while allowing for rotation of valve disk 132 from a closed position to an open position as tabs 222, 224 of cap plate 168 engage slots 120.

In some embodiments, located within the central axis 18 of base plate 164 is a port 237. Port 237 receives tubing 48. Tubing 48 extends from a space on the outside surface 16 of cap plate 168 through opening 170 into the interior space defined by manifold cage 158. The tubing may be formed of a rigid or flexible material, including for example, plastic or silicone. Tubing 48 further extends through port 237 in base plate 164 and exits on the outside surface 12 of base plate 164. Tubing 48b extends outwardly from cap plate 168 and is optionally joined with a filter assembly 194. Tubing 48a extends outwardly from base plate 164 where it is joined with boss 136. Tubing 48, 48a, 48b provides fluid communication from filter assembly 194 through the manifold and through bore 138 and conduit 56. Port 237 and opening 170 are dimensioned to receive tube 48 which in turn is sized to receive valve disk boss 136. Further, the diameter of tubing 48 is sized so that it fits around boss 136 with a fluid tight, friction fit. In other embodiments, the diameter of tubing 48 is sized so that it fits into boss 136 with a fluid tight, friction fit. The tube 48 may be connected with the cage 158 by compression fit, adhesive, or any other appropriate connection method.

Because port 237 is centrally located within base plate 164 and opening 170 is off center of the central axis of cap plate 168, tubing 48 extends through manifold cage 158 at an angle. As a result, when manifold 46 is removably coupled within manifold receiver 44, port 237 and opening 170 are located on different parallel axes.

Figure 7:
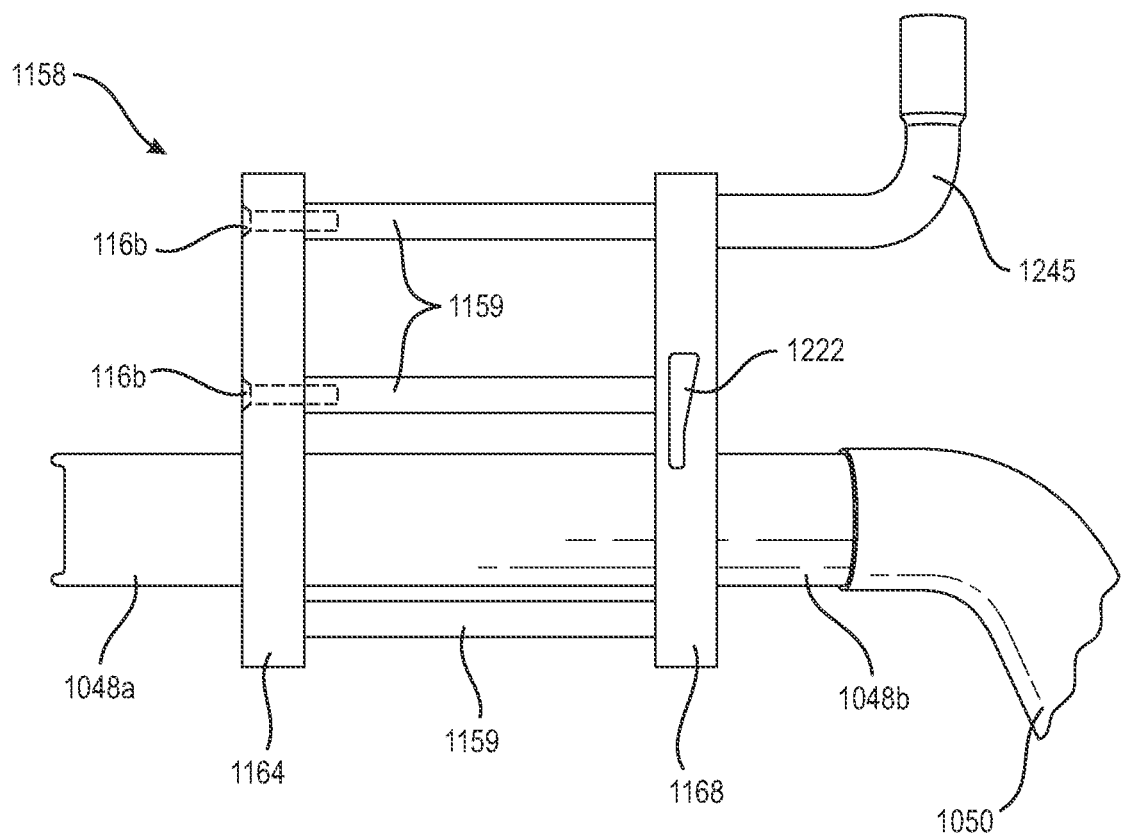
FIG. 7 is a side elevation view of an alternative embodiment of the manifold cage.
Figure 13:
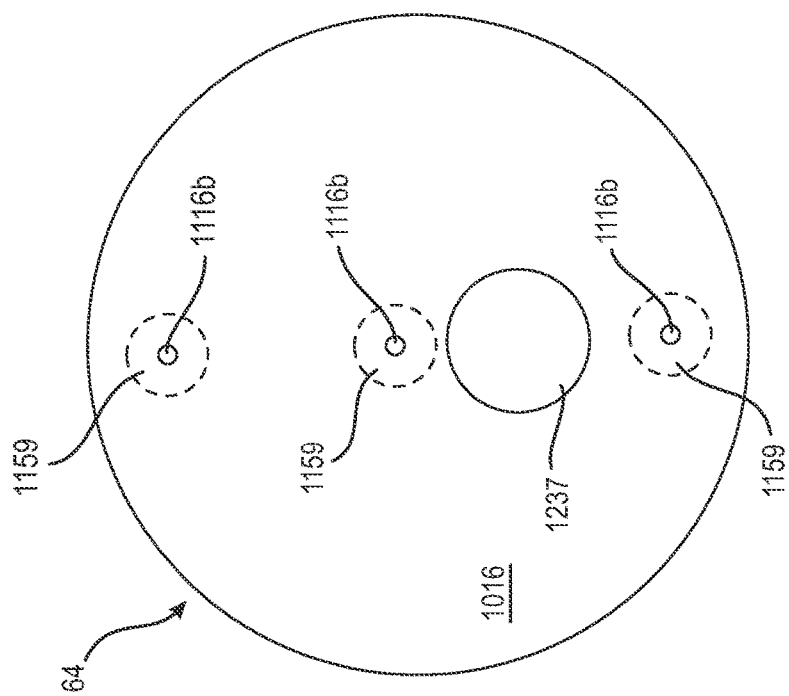
FIG. 13 is a bottom view of the manifold cage base plate of FIG. 7.
Figure 12:
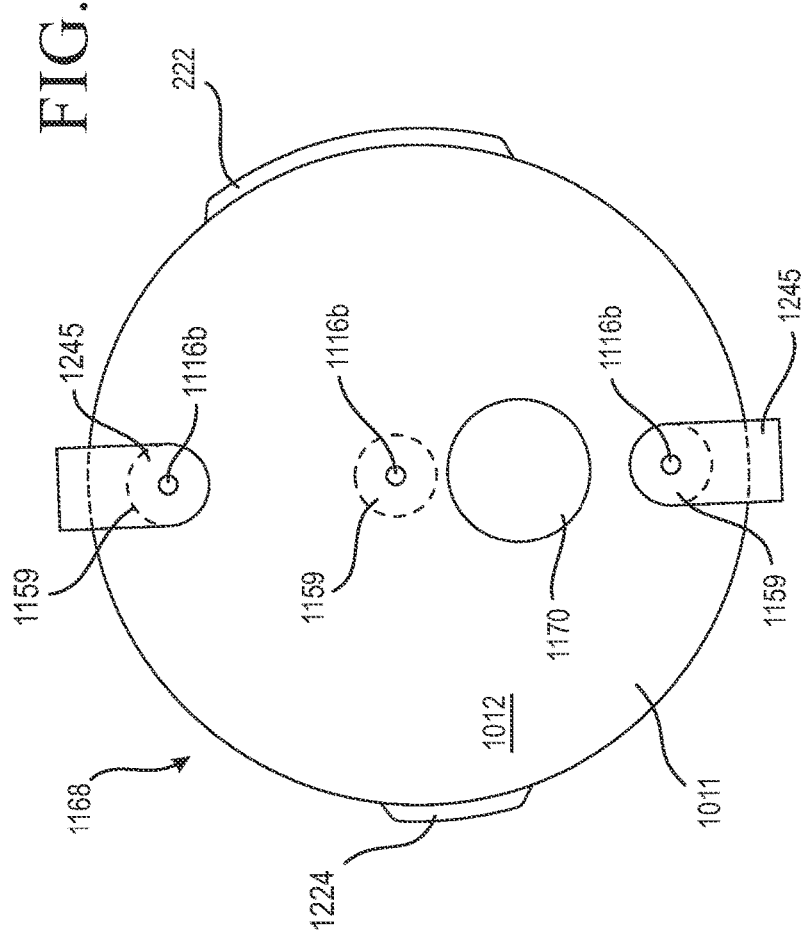
FIG. 12 is a top view of the manifold cage cap plate of FIG. 7.

In an alternative embodiment depicted in FIGS. 7, 12 and 13 manifold cage 1158 includes cap plate 1168, tabs 1222, base plate 1164 and a plurality of ribs 1159. Features and construction of manifold cage 1158 are substantially similar to features and construction of manifold cage 158, with the exception being port 1237 of base plate 1164. Port 1237 is centered along an axis that is off center to the longitudinal axis 1018 of the cage 1158. When assembled, port 1237 and opening 1170 share the same axis and are located along the same plane.

Prior to use, before the manifold 46 is fitted to the mobile unit 30, manifold receiver 44 is in the state as depicted in FIG. 5. Specifically, valve disk 132 is in the index position so that the body of the valve disk is closed over the opening in plate 96 to receiver adapter conduit 56.

Mobile unit 30 is prepared for use by fitting the manifold 46 to the complementary receiver 46 associated with the canister 36 or 38 in which the waste drawn from the surgical site is to be collected. This step is performed by inserting the manifold 46 into the receiver so that manifold base plate 164 is directed to the valve disk 132. For mobile unit 30 to function, valve disk boss 136 must seat in tubing 48a exiting from port 237. Lock ring slots 120 and tabs 222 and 224 cooperate to ensure this alignment of the manifold 46 to the valve disk 132. Specifically, these components are positioned so positioning of manifold tab 222 in receiver slot 120 results in the manifold 46 being rotationally positioned so that port 237 and tubing 48a are aligned with valve disk boss 136. Proper alignment and insertion of manifold 46 into the receiver housing 62 results in tube 48a fitting over the valve disk boss 136.

Once the manifold 46 is joined with valve disk 132, the manifold is rotated. The direction of rotation is dictated by the fact that tabs 222 and 224 can only rotate into receiver 44 lock ring slots 122. As a consequence of the rotation of the manifold, the valve disk boss 136 and, by extension, the whole of the valve disk 132, undergoes a like rotation. This rotation places valve bore 138 in registration with the receiver adaptor distal end opening into conduit 58. Also, as result of the rotation of the manifold 46 and the valve disk 132, the manifold is positioned so that manifold port 237 is, in a rotational position, at the bottom of the manifold. Consequently, tubing 48 extends on a downward slope from an area outside the manifold, through manifold cage 158 and to the connection with bore 138.

Thus, tubing 48a at port 237 functions as a keyhole for receiving valve disk boss 136. Valve disk boss 136 functions as a drive member that rotates the valve disk 132 to the open state. The rotation of the manifold 46 results in more than a like rotation of valve disk 132. From the above discussion, it should be clear that when the manifold is seated in the receiver housing, tube 48a extends over valve boss 136. As the manifold 46 is rotated, surfaces 123 internal to the lock ring 66 function as cam surfaces against which manifold tabs 222 and 224 abut. These surfaces 123 are directed proximally rearward. Therefore, as the manifold turns, the abutment of the tabs 222 and 224 against the proximally directed surfaces 123 results in the manifold being driven in the like proximal direction. This action results in sufficient force being generated to overcome the elastomeric forces thus pushing tube 48a down over the valve boss 136.

The process of preparing the mobile unit 30 for use is completed by the coupling of a suction applicator 52 to the unit by a suction line 50. Mobile unit 30 is actuated by activating the suction pump 58. Activation of suction pump 58 results in a waste stream being drawn from the surgical site being drawn into the applicator 52, through the suction line 50 into optional filter basket 166 and into tubing 48b. This waste stream includes liquid and solid waste to which the suction applicator 52 is applied as well as air adjacent the applicator 52. Solid waste contained in the waste stream is trapped by the filter basket 166. The suction force draws the components of the waste stream that flows past the filter basket 166 into tube 48 which extends through manifold cage 158 into the open proximal end of bore 138 integral with valve disk 132. Boss 136 serves as the fitting through which the waste stream flows from the manifold 46 into conduit 58. The barrier formed by the connection between tube 48a and valve boss 136 prevents loss of vacuum between these components.

From valve disk bore 138 the waste stream flows through the receiver adapter conduit 58 into the associated canister 36 or 38. Liquid and solid components of the waste stream that enter the canister 36 or 38 precipitate out of the stream and are held in the canister 36 and 38 for final disposal.

In embodiments including the filter basket, the fluid stream that travels from the canister 36 or 38 is thus essentially liquid and solid free. Prior to final exhaust of this stream from the suction pump 58, this fluid stream is filtered to remove odor causing components and/or bacterial and viral sized particulates that may be entrained in this fluid stream.

Once the medical/surgical procedure is completed, and use of the mobile unit 30 is no longer required, manifold 46 is removed. The seating of manifold tabs 222 and 224 in the lock ring slots 122 prevents the manifold 46 from being pulled out of the receiver 44. Instead, it is necessary to first rotate the manifold 46 so that tabs 222 and 224 align in slots 120. As a consequence of having to so rotate the manifold 46, the valve disk 132 undergoes a like rotation. The rotation of the valve disk 132 reorients the disk so the disk again covers the open end of the receiver adapter conduit 58. Once manifold 46 is properly positioned, the manifold is manually withdrawn from the receiver 44. With valve disk 132 reoriented, port 237 is now positioned in vertical spaced relation above opening 170. Consequently, tubing 48 extends on a downward slope as it exits the manifold on an outside surface 126 of cap plate 168. Any fluid remaining within the manifold may drain away from port 237 through tube 48 and into tube 48b where it returns to and is captured by the filter basket. The manifold may include tube caps a one or both ends to prevent fluid leakage after use or debris collection prior to use.

In certain embodiments, manifold 46 is further designed so that when the manifold seats over the valve boss 136, tube 48a is joined to the outer surface of the boss. Owing to the camming action of the manifold tabs 222 and 224 within slots 122, displacement is a result of the application of the rotational "twisting" of the manifold in position. The physical effort one needs to exert when so rotating the manifold for both insertion and removal does not impose an appreciable strain on the arm or hand of the user. In addition, owing to the friction fit between tube 48a and boss 136, there is essentially no air flow around these seal-forming components. The absence of this air flow means these components do not engage in a vibrational movement that results in the generation of noise.

In further embodiments of the invention, the cross sectional area of the valve disk bore 138 is at least equal to the cumulative cross sectional areas of tubing 48. Thus, as the waste stream flows through the manifold 46, the gaseous components of this stream do not engage in noise-generating compression. Further since the gas flow is not compressed, the flow of the fluid into bore 138 does not result in drop in flow rate.

The geometry and orientation of the manifold receiver 44 also reduces the leakage of waste from both the mobile unit 30 and the manifold 46. As mentioned above, the receiver adapter 64 is designed so that plate 96 is angularly offset from the vertical. Consequently, receiver housing 62 is angled from the horizontal. By extension, when the manifold 46 is seated in the receiver housing 62, the manifold is similarly offset from the horizontal. More specifically, when fitted within receiver 44, manifold base plate 164 is angled from horizontal and in spaced relation below the manifold cap plate 168. This means that when the manifold 46 is in the run position, port 237 is located at the lowest elevation of the manifold. This feature ensures that substantially all waste material drawn into the manifold flows out through the valve disk bore 138 and adapter conduit 58 into the canister 36 or 38.

Then, when the manifold 46 is rotated for removal from receiver 44, valve disk 132 is rotated upwardly into a closed position and port 237 is now located in vertical spaced relation above opening 170. Waste material still in the manifold may flow back towards cap plate 168 and exits into tube 48b where it returns to and is captured by the filter basket. Thus, upon removal of the manifold 46 from the receiver 44, waste still in the manifold may be moved away from opening 170. This reduced the instances of this waste leaking from the opening.

The above angled orientation of the manifold receiver 44 also ensures that, when the mobile unit 30 is in operation, the proximal end base manifold outlet port 237 is, in a gravity orientation, below inlet opening 170. This makes it unlikely that waste in the manifold can flow upstream, through opening 170, and out the manifold 46.

Owing to the manifold 46 having a cage like structure 158, medical personnel are provided with a quick means to verify that the manifold being fitted to the mobile unit 30 is not a used manifold that contains previously collected waste.

Features other than tabs may be integral with the manifold to ensure that the manifold when inserted into the receiver, manifold port 237 is aligned with the valve disk boss 136 and bore 138. Thus, in an alternative version of the invention, the manifold is formed with one or more slots or other void spaces along the outer surface thereof. These slots receive alignment pins integral with the manifold receiver. In these versions of the invention, the surfaces of the manifold that define these slots may also function as cam surfaces. Thus, as the manifold is inserted in the receiver, the manifold is urged off these static alignment pins further into the receiver.

Likewise, in an alternative version of the invention, the camming surfaces that, upon manifold rotation, urge the manifold proximally rearward may not be on the manifold receiver. In some versions of the invention, the alignment tabs, grooves or notches integral with the manifold may have angled or tapered profiles. As the manifold is rotated, the abutment of these surfaces against fixed surfaces integral with the receiver, result in the manifold being moved proximally. Further, in some versions of the invention, there is only a single camming surface integral with the receiver and/or manifold.

Figure 14:
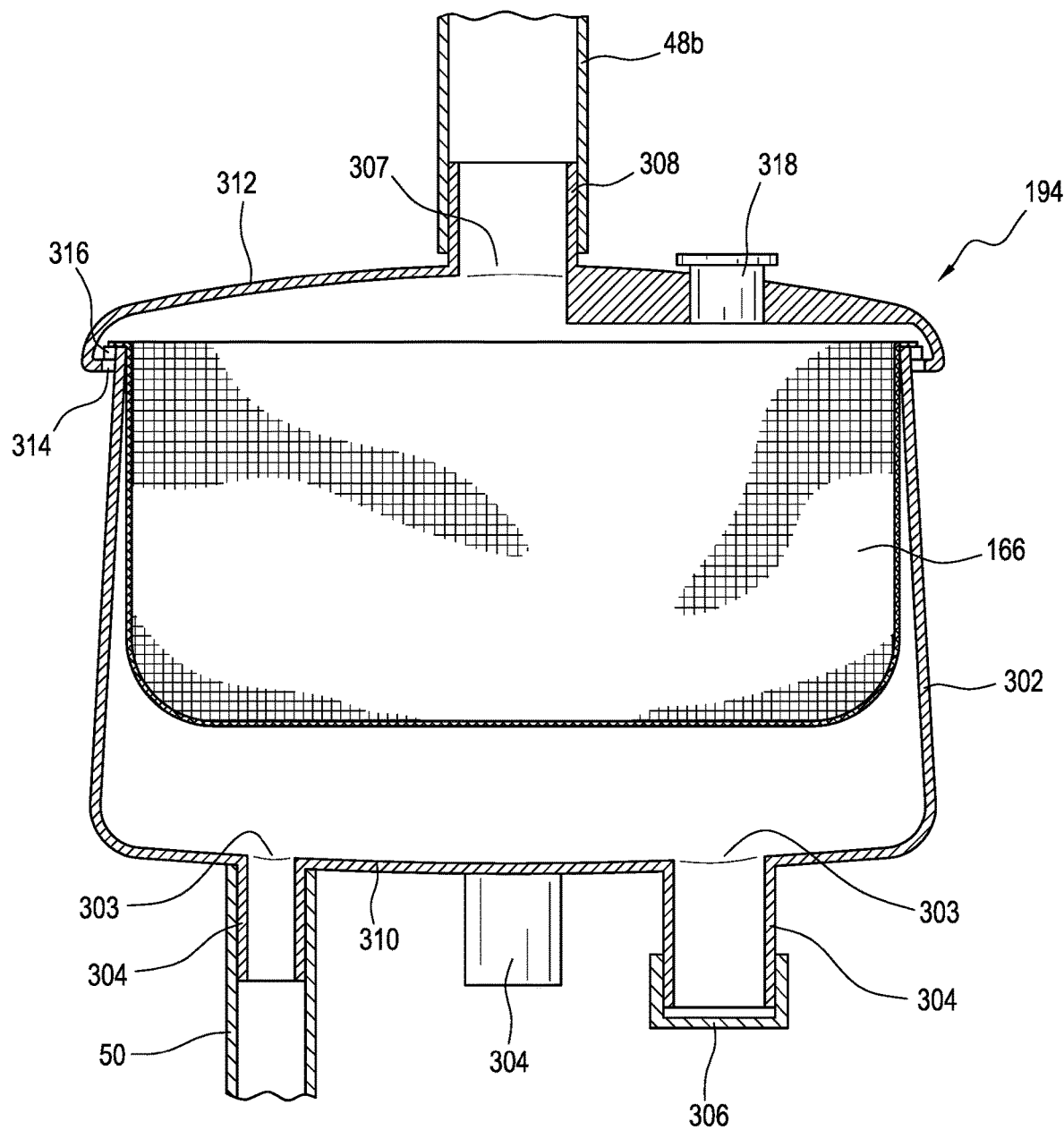
FIG. 14 is a cut-away, side view of a filter assembly in accordance with embodiments of the present invention.

FIG. 14 illustrates a filter assembly 194 in accordance with further embodiments of the invention. The filter assembly comprises a filter housing 302. The filter housing may comprise one or more inlets 303 that provide for connection of suction lines 50. In particular, the inlets 303 may be adapted to provide a press fit of suction line 50 over an inlet boss 304. Alternatively, other forms of connection may be used. Multiple inlets may be provided such that multiple suction lines can be attached to a single filter assembly with inlet caps 306 positioned on inlets that are not in use. For example, a filter assembly may provide four inlets. Caps may be placed on unused inlets such that the filter assembly may be used with one to four suction lines. The inlets may be formed in a lower surface 310 of the housing 302. Alternatively, the housing may be oriented in a different manner such that the inlets 304 are formed through a side or top surface.

The filter assembly may further comprise an assembly lid 312 that seals the filter assembly in a liquid tight manner. The lid 312 may include engagement elements 314 that engage with corresponding elements 316 formed or attached to the filter housing 302. Additionally, a seal may be placed between the housing and lid.

The filter assembly 194 further compromises an outlet 307. The outlet may be adapted to connect with the tubing 48b that extends from the manifold adapter by means of an outlet boss 308. The outlet boss 308 may be adapted to connect with the tubing 48 by press fit or by other appropriate mechanisms, such as a hose clamp, threads, bayonet fitting, or the like. The outlet 307 may extend through a top surface of the lid 312. Alternatively, the housing may be oriented in a different manner such that the inlets 304 are formed through a side or top surface.

The filter assembly may further comprise a filter element. The filter element may be a filter basket 166. The filter basket may be adapted to filter and collect bone fragments, tissue or other debris collected through the suction line 50. Simultaneously, the filter basket may allow fluids and/or smaller solid fragments to pass through the filter assembly to a canister of the waste collection system. The filter basket may comprise slats, mesh, perforations, or any other appropriate filtering structure or material and may, for example, be formed of plastic, metal, foam or some combination. The filter basket may have a generally cylindrical shape with a closed bottom surface, as illustrated in FIG. 14. Alternatively, the filter basket need not have a "basket" shape and may be flat, conical, convex, concave, or any other shape as would be understood by one of ordinary skill in the art.

Further embodiments of the filter assembly may include a pressure release valve 318. The pressure release valve may be positioned in the filter assembly downstream of the filter basket. When the valve is actuated, it allows the suction path to temporarily bypass the filter basket 166. This suction bypass allows material collected on the filter basket to release from the surface of the filter and thereby prevents or reduces clogging of the filter and resultant reduction of the suction force. The valve 318 may take the form of a button that is pressed by the user as illustrated in FIG. 14.

While the present invention has been described with reference to one or more particular embodiments, those skilled in the art will recognize that many changes may be made thereto without departing from the spirit and scope of the present invention. Furthermore, components form one embodiment can be used in other non-exclusive embodiments. Each of these embodiments and obvious variations thereof is contemplated as falling within the spirit and scope of the invention. Thus, there is no requirement that each of the above described features be incorporated in all versions of the invention.

What is claimed is:

1. A manifold assembly for use with a waste collection system comprising:
   a manifold that is inserted into a manifold receiver of the waste collection system, the manifold comprising:
      a circular base plate comprising an outlet port extending through the base plate,
      a circular cap plate spaced apart from the base plate and comprising an inlet opening extending through the cap plate, and
      a tube connecting the base plate port with the cap plate opening such that waste collected by the waste collection system flows into the manifold through the cap plate opening, through the tube, and out of the manifold through the base plate port when the manifold is in use; and
   a filter assembly comprising:
      a filter housing,
      a filter basket, and
      an outlet fluidly connected with the manifold tube;
   wherein the outlet port of the manifold engages a valve of the waste collection system such that the valve is open when the manifold is fully inserted into the manifold receiver and the valve is closed when the manifold is removed from the manifold receiver.

2. The manifold assembly of claim 1 wherein inserting the manifold opens the valve by actuating a valve disk of the valve.

3. The manifold assembly of claim 2 wherein the manifold outlet port engages a boss extend from the valve disk.

4. The manifold assembly of claim 2 wherein rotating the manifold during insertion rotates the valve disk.

5. The manifold assembly of claim 1 wherein the manifold further comprises a tab.

6. The manifold assembly of claim 5 wherein the tab engages a receiver slot formed in the manifold receiver.

7. The manifold assembly of claim 6 wherein an initial engagement between the tab and the receiver slot aligns the manifold base plate with a valve disk of the valve.

8. The manifold assembly of claim 6 wherein the manifold is rotated to fully engage the tab with the receiver slot.

9. The manifold assembly of claim 8 wherein the rotation of the manifold rotates the valve disk.

10. A manifold assembly for use with a waste collection system comprising:
    a manifold that is inserted into a manifold receiver of the waste collection system, the manifold comprising:
       a circular base plate comprising an outlet port extending through the base plate,
       a circular cap plate spaced apart from the base plate and comprising an inlet opening extending through the cap plate,
       a tube connecting the base plate port with the cap plate opening such that waste collected by the waste collection system flows into the manifold through the cap plate opening, through the tube, and out of the manifold through the base plate port when the manifold is in use, and
       a rib connecting the base plate with the cap plate; and
    a filter assembly comprising:
       a filter housing,
       a filter basket, and
       an outlet fluidly connected with the manifold tube;
    wherein the base plate, the cap plate, and the rib of the manifold form a cage having closed ends and an open side; and
    wherein the outlet port of the manifold engages a valve of the waste collection system such that the valve is open when the manifold is fully inserted into the manifold receiver and the valve is closed when the manifold is removed from the manifold receiver.

11. The manifold assembly of claim 10 wherein the tube is accessible when the manifold has not been inserted into the manifold receiver.

12. The manifold assembly of claim 11 wherein the tube is not accessible when the manifold has been inserted into the manifold receiver.

13. The manifold assembly of claim 10 wherein the manifold further comprises a second rib.

14. The manifold assembly of claim 13 wherein the base plate comprises an inside surface and the cap plate comprises an inside surface.

15. The manifold assembly of claim 14 wherein the base plate inside surface is parallel to the cap plate inside surface and the first rib is parallel to the second rib.

16. A manifold assembly for use with a waste collection system comprising:
    a manifold that is inserted into a manifold receiver of the waste collection system, the manifold comprising:
       a circular base plate comprising an outlet port extending through the base plate,
       a circular cap plate spaced apart from the base plate and comprising an inlet opening extending through the cap plate,
       a tube connecting the base plate port with the cap plate opening,
       a first rib connecting the base plate with the cap plate, and
       a second rib connecting the base plate with the cap plate; and
    a filter assembly comprising a filter housing;
    wherein the tube is oblique to the first rib.

17. The manifold assembly of claim 16 wherein the base plate is parallel to the cap plate.

18. The manifold assembly of claim 17 wherein the first rib is parallel to the second rib.

* * * * *